US011337763B2

(12) United States Patent
Choi

(10) Patent No.: US 11,337,763 B2
(45) Date of Patent: May 24, 2022

(54) C-ARM-BASED MEDICAL IMAGING SYSTEM, AND METHOD FOR MATCHING 2D IMAGE AND 3D SPACE

(71) Applicant: CUREXO, INC., Seoul (KR)

(72) Inventor: Jin Hyeok Choi, Gwangju-si (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 17/437,608

(22) PCT Filed: Mar. 13, 2020

(86) PCT No.: PCT/KR2020/003564
§ 371 (c)(1),
(2) Date: Sep. 9, 2021

(87) PCT Pub. No.: WO2020/185048
PCT Pub. Date: Sep. 17, 2020

(65) Prior Publication Data
US 2022/0039874 A1    Feb. 10, 2022

(30) Foreign Application Priority Data

Mar. 13, 2019    (KR) .......................... 10-2019-0028592

(51) Int. Cl.
*A61B 34/20* (2016.01)
*A61B 90/00* (2016.01)
*A61B 6/00* (2006.01)

(52) U.S. Cl.
CPC .............. *A61B 34/20* (2016.02); *A61B 90/37* (2016.02); *A61B 90/39* (2016.02); *A61B 6/4441* (2013.01);

(Continued)

(58) Field of Classification Search
CPC ......... A61B 34/20; A61B 90/37; A61B 90/39; A61B 2034/2055; A61B 2034/2065;
(Continued)

(56) References Cited

U.S. PATENT DOCUMENTS

2017/0273595 A1    9/2017  Lee
2017/0319156 A1   11/2017  Hong et al.

FOREIGN PATENT DOCUMENTS

KR    10-2007-0045023 A    5/2007
KR    10-2015-0099375 A    8/2015
(Continued)

*Primary Examiner* — Amelie R Davis
(74) *Attorney, Agent, or Firm* — Novick, Kim & Lee, PLLC; Jae Youn Kim; Jihun Kim

(57) ABSTRACT

Proposed is a medical imaging system including: a C-arm including an X-ray source and a detector; a first plate installed on an X-ray path between the X-ray source and the detector, and including a first transmissive surface provided with a plurality of first ball markers blocking an X-ray, and a first optical marker; a second plate installed on the X-ray path between the X-ray source and the detector, and including a second transmissive surface provided with a plurality of second ball markers blocking the X-ray, and a second optical marker; a reference optical marker configured to provide a 3D reference coordinate system; an optical tracking device configured to recognize locations of the first and second optical markers and the reference optical marker; and a matcher configured to calculate a matching relationship between coordinates on a 3D reference coordinate system and locations on first and second captured images.

14 Claims, 8 Drawing Sheets

(52) U.S. Cl.
CPC ............ *A61B 2034/2055* (2016.02); *A61B 2034/2065* (2016.02); *A61B 2034/2068* (2016.02); *A61B 2090/367* (2016.02); *A61B 2090/3764* (2016.02)

(58) Field of Classification Search
CPC ...... A61B 2034/2068; A61B 2090/367; A61B 2090/3764
See application file for complete search history.

(56) References Cited

FOREIGN PATENT DOCUMENTS

| | | | |
|---|---|---|---|
| KR | 10-2016-0034104 | A | 3/2016 |
| KR | 10-2017-0124962 | A | 11/2017 |
| KR | 10-2018-0119361 | A | 11/2018 |
| WO | 15126205 | A2 | 8/2015 |

C-ARM-BASED MEDICAL IMAGING SYSTEM, AND METHOD FOR MATCHING 2D IMAGE AND 3D SPACE

TECHNICAL FIELD

The disclosure relates to a C-arm-based medical imaging system and a method of matching a 2D image and a 3D space, and more particularly to a medical imaging system and method for creating a matching relationship between C-arm image pixels and corresponding 3D space coordinates and/or a matching relationship between arbitrary 3D coordinates and corresponding C-arm image pixels.

BACKGROUND ART

A C-arm-based medical imaging system has contributed significantly to high accuracy in treatment by allowing a medical doctor to check treatment status in real time. For example, when a surgical procedure for epidural injection, nerve block, neuroplasty, radiofrequency thermal ablation, or the like known as spinal disc treatment is performed, a medical doctor checks a C-arm image with his/her naked eyes while giving an injection and introducing a catheter into a lesion around a spinal nerve, thereby guaranteeing the safety and accuracy of the surgical procedure.

With development of a medical robot, a planning system, a navigation system, and the like for assisting a medical doctor to perform a surgical procedure, the medical robot, the planning system and the like are required to have advanced functions, for example, 3D reconstruction of a C-arm-scanned object, 3D spatial-location information about a subject, etc. However, a common C-arm does not provide such functions.

As disclosed in FIG. 1, a mobile C-arm X-ray apparatus generally includes an X-ray source 100, a detector 200 facing the X-ray source 100, a C-shaped frame 300, and an actuator 400 for moving the frame 300. A surgical operator controls the actuator 400 to rotationally or translationally move the frame 300 and location the source 100 and the detector 200 at desired capturing locations, and obtains an image by emitting an X-ray. The surgical operator may obtain a plurality of X-ray images of a subject 500 while changing the locations of the source 100 and the detector 200, and reconstruct 3D voxels by a so-called 'back-projection'.

However, it is impossible to not only reconstruct accurate voxels but also provide location information about the voxels because the geometric structure of the C-arm apparatus does not provide accurate location information. The C-arm X-ray source 100 is very heavy and thus likely to sag, and therefore the geometric structure of the C-arm is not constantly maintained even though the source 100 and the detector 200 are rotationally moved along a circumferential track of the frame 300. Accordingly, it is difficult to reconstruct the accurate voxels based on the 'back-projection'. Further, none other than the manufacturer can know the location of the detector plane d 202 because the detector plane d 202 is located inside a C-arm, and the exact location of the light source is unknown because the source apparatus S 102 is located inside the case. Accordingly, it is impossible to specify an actual location of a merged 3D model based on the C-arm images.

Hence, there has been required technology for a new medical imaging system in which only information about a given C-arm geometric structure is enough to match an image and a space.

DISCLOSURE

Technical Problem

Accordingly, the disclosure is conceived to solve the foregoing problems of the related art, and an aspect of the disclosure is to provide a medical imaging system and method for matching desired C-arm image pixels and medical space coordinates corresponding to the image pixels without forming 3D voxels. Further, the disclosure is to provide a medical imaging system and method for matching arbitrary medical space coordinates with certain pixels on a given C-arm image.

Technical Solution

According to an aspect of the disclosure, there is provided a medical imaging system including: a C-type fluoroscopy device (hereinafter, referred to as 'C-arm') including an X-ray source and a detector; a first plate installed on an X-ray path between the X-ray source and the detector, and including a first transmissive surface provided with a plurality of first ball markers blocking an X-ray, and a first optical marker; a second plate installed on the X-ray path between the X-ray source and the detector, and including a second transmissive surface provided with a plurality of second ball markers blocking the X-ray, and a second optical marker; a reference optical marker configured to provide a 3D reference coordinate system; an optical tracking device configured to recognize locations of the first and second optical markers and the reference optical marker; and a matcher configured to calculate a matching relationship between coordinates on a 3D reference coordinate system and locations on first and second captured images, based on the first and second captured images respectively obtained by the detector with regard to a subject at first and second locations, locations of the first and second ball markers on the first and second captured images, and location information obtained by the optical tracking device.

Here, the matcher may be configured to obtain first and second projected images by respectively projecting the first and second captured images to the first plate along the X-ray path, based on a matching relationship between the location of the first ball marker on the first and second captured images; and the location of the first ball marker on the first plate calculated using the first optical marker, and may be configured to obtain first and second source locations of the X-ray source respectively corresponding to the first and second captured images, based on a matching relationship between the location of the second ball marker on the first and second projected images; and the location of the second ball marker on the second plate calculated using the second optical marker. Further, the matcher may be configured to calculate a 3D imaging space in which a projection path of a first X-ray emitted at the first source location from a location relationship between the first source location and the first projected image overlaps a projection path of a second X-ray emitted at the second source location from a location relationship between the second source location and the second projected image.

The medical imaging system may further include: a display configured to display the first and second captured images; and a user interface configured to receive information about certain locations on the first and second captured images from a surgical operator, wherein the matcher may be configured to calculate spatial coordinates in the reference coordinate system, which correspond to the location information input by the surgical operator.

The medical imaging system may further include a medical instrument including a third optical marker, wherein the matcher may be configured to obtain location coordinates of the medical instrument obtained by the optical tracking device using the third optical marker, and calculate location information about the medical instrument on the first and second captured images based on a transformation relationship.

Further, the first plate may include a fastening member to be fastened to the C-arm so that the first transmissive surface can be located in front of the detector, and the second plate may be installed between the first plate and the X-ray detector.

According to another aspect of the disclosure, there is provided a method of matching a C-arm 2D image and a 3D space, including: obtaining a first captured image at a first location by a C-arm detector; obtaining a first projected image by projecting the first captured image back to a first plate along a first X-ray path corresponding to the first location, in which the first plate is provided on the first X-ray path and includes a first optical marker of which a location is identifiable in a medical spatial coordinate system (hereinafter, referred to as a 'reference coordinate system'); calculating a location of a C-arm source corresponding to the first location, i.e., a first source location, based on a matching relationship between a location on the reference coordinate system of a ball marker of a second plate provided on the first X-ray path and a location of the ball marker of the second plate on the first projected image; obtaining a second captured image at a second location by the C-arm detector; obtaining a second projected image by projecting the second captured image back to the first plate provided on a second X-ray path along the second X-ray path corresponding to the second location; calculating a location of the C-arm source corresponding to the second location, i.e., a second source location, based on a matching relationship between a location on the reference coordinate system of the ball marker of the second plate provided on the second X-ray path and a location of the ball marker of the second plate on the first projected image; and calculating coordinates of an intersection between a first line connecting the first source location and a first pixel on the first projected image and a second line connecting the second source location and the second pixel on the second projected image.

Further, according to still another aspect of the disclosure, there is provided a method of matching a C-arm 2D image and a 3D space, including: obtaining a first captured image at a first location by a C-arm detector; obtaining a first projected image by projecting the first captured image back to a first plate along a first X-ray path corresponding to the first location, in which the first plate is provided on the first X-ray path and includes a first optical marker of which a location is identifiable in a reference coordinate system; calculating a location of a C-arm source corresponding to the first location, i.e., a first source location, based on a matching relationship between a location on the reference coordinate system of a ball marker of a second plate provided on the first X-ray path and a location of the ball marker of the second plate on the first projected image; obtaining a second captured image at a second location by the C-arm detector; obtaining a second projected image by projecting the second captured image back to the first plate provided on a second X-ray path along the second X-ray path corresponding to the second location; calculating a location of the C-arm source corresponding to the second location, i.e., a second source location, based on a matching relationship between a location on the reference coordinate system of the ball marker of the second plate provided on the second X-ray path and a location of the ball marker of the second plate on the first projected image; and calculating first pixels to which certain spatial coordinates are projected on the first projected image along the first X-ray path, and calculating second pixels to which the certain spatial coordinates are projected on the second projected image along the second X-ray path.

Here, the obtaining the first projected image of the first captured image on the first plate may include calculating the first projected image by warping the first captured image based on a location on the first captured image corresponding to the ball marker of the first plate and a location on the reference coordinate system. Further, the obtaining the second projected image of the second captured image on the first plate may include calculating the second projected image by warping the second captured image based on a location on the second captured image corresponding to the ball marker of the first plate and a location on the reference coordinate system.

Advantageous Effects

According to the disclosure, it is possible to derive a matching relationship between image pixels and spatial coordinates from a correlation between the minimum number of C-arm images, in other words, the C-arm images obtained at two arbitrary locations, thereby achieving planning and navigation functions for surgical operation based on the spatial coordinates using the minimum number of C-arm images regardless of locations without forming a 3D voxel.

MODE FOR INVENTION

Below, embodiments of the disclosure will be described with reference to the accompanying drawings.

Figure 1:
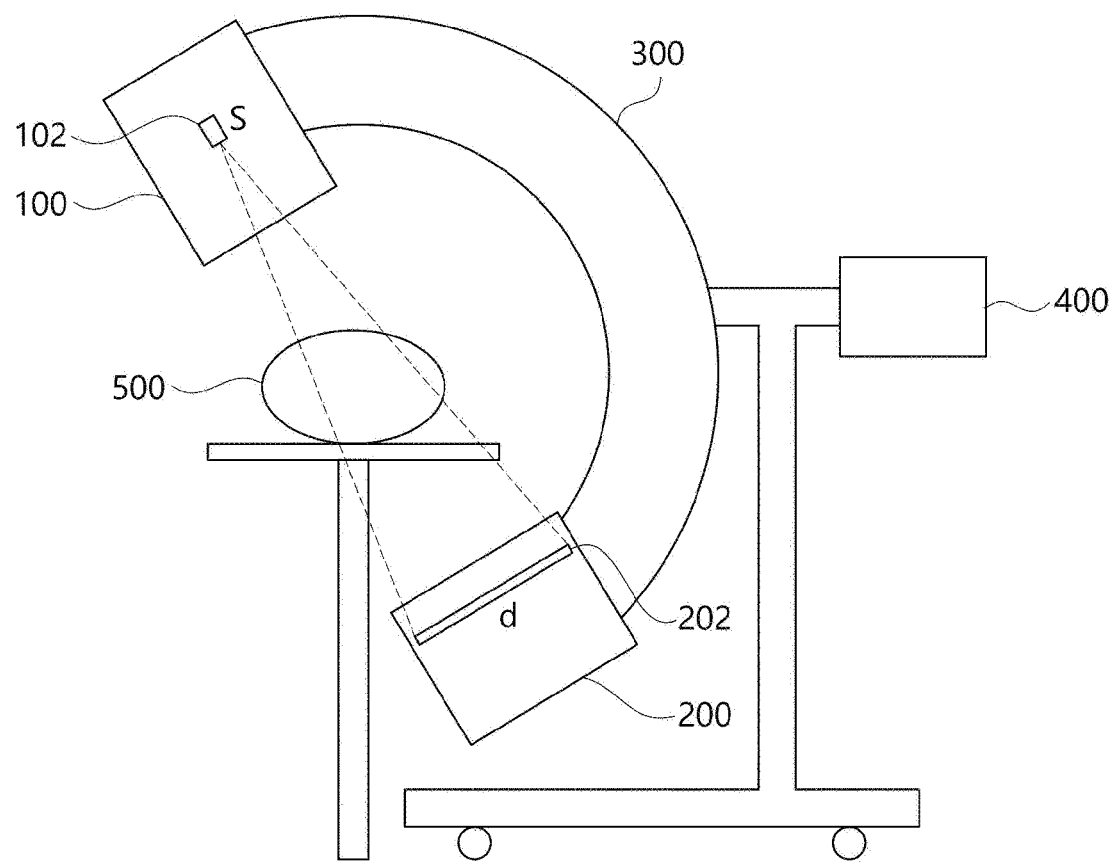
FIG. 1 is a schematic structure view of a conventional C-arm apparatus.
Figure 2:
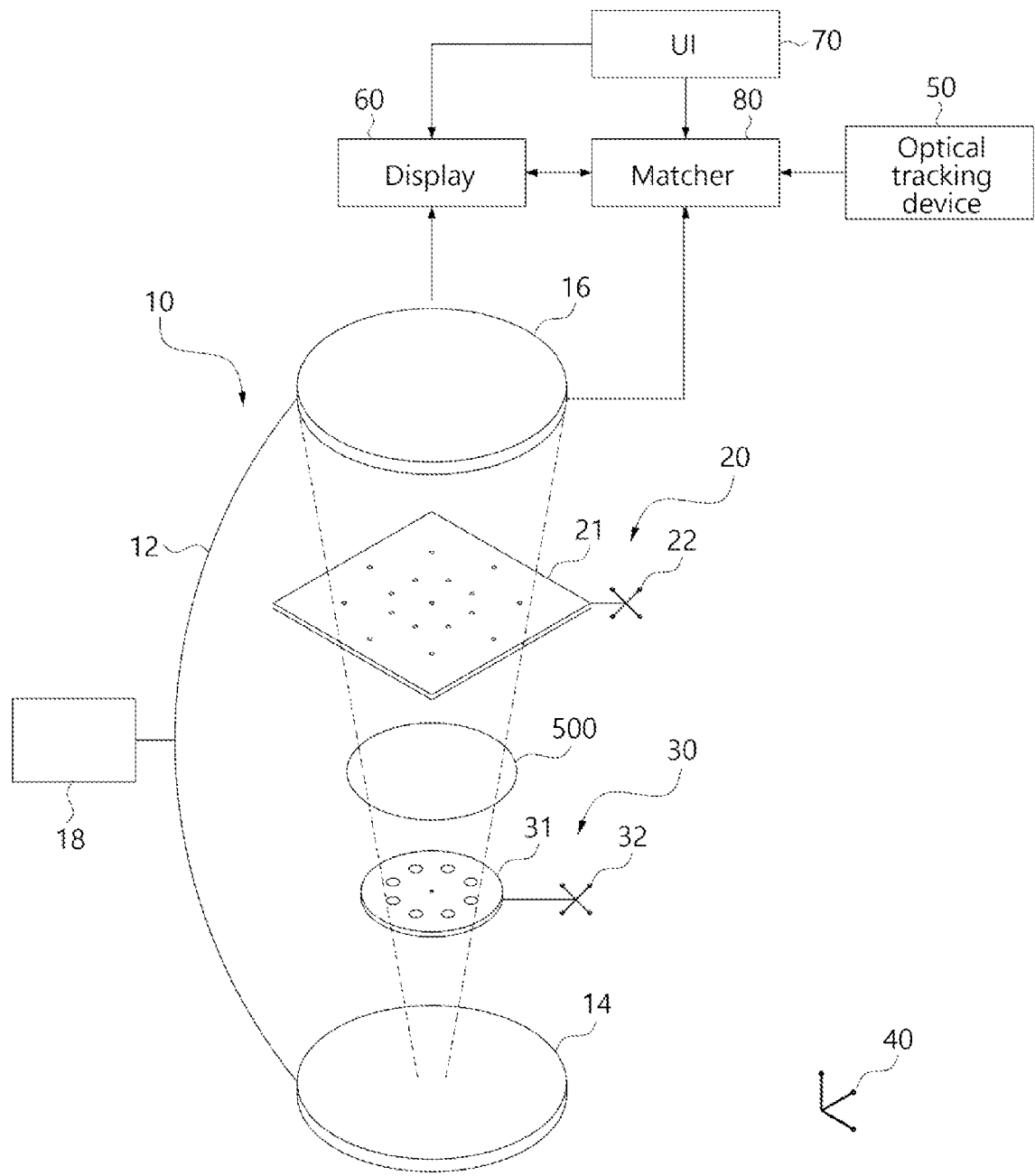
FIG. 2 is a schematic view of a C-arm-based medical imaging system according to an embodiment of the disclosure.

FIG. 2 is a schematic view of a C-arm-based medical imaging system according to an embodiment of the disclosure.

Referring to FIG. 2, the C-arm-based medical imaging system according to an embodiment of the disclosure includes a C-arm 10, a first plate 20, a second plate 30, a reference optical marker 40, an optical tracking device 50, a display 60, a user interface 70, and a matcher 80.

The C-arm 10 is provided with an X-ray source 14 and a detector 16 which are installed at opposite ends of a frame 12 and face each other, and includes an actuator 18 for rotationally or translationally moving the frame 12.

The first plate 20 includes a first transmissive surface 21 on which a plurality of first ball markers are formed drawing a first pattern, and a first optical marker 22. Here, the first transmissive surface 21 is installed to intersect an X-ray path between the X-ray source 14 and the detector 16 of the C-arm 10, the first ball marker is made of an X-ray blocking material. The first optical marker 22 is provided to define a coordinate system for the first plate 20, and be also detected by an external optical tracking device.

The first plate 20 may be stationarily installed in the C-arm 10 so that the first plate 20 can be located on a first X-ray path when the C-arm source 14 and the detector 16 are in a first location to capture an image, but located on a second X-ray path when the locations of the source 14 and the detector 16 are changed to a second location to capture an image. For example, the first plate 20 may include a fastening member (not shown) so as to be fastened to the front surface of the detector 16.

The second plate 30 includes a second transmissive surface 31 on which a plurality of second ball markers are formed drawing a second pattern, and a second optical marker 32. The second transmissive surface 31 is installed to intersect an X-ray path between the X-ray source 14 and the detector 16 of the C-arm 10, and the second ball marker is made of an X-ray blocking material. The second optical marker 32 is provided to define a coordinate system for the second plate 30, and be also detected by an external optical tracking device.

The second plate 30 may be stationarily or semi-stationarily installed to intersect the first X-ray path and the second X-ray path corresponding to the first and second locations, like the first plate 20.

The reference optical marker 40 is to provide a reference for defining a coordinate system of a medical space in which the C-arm 10 operates, and is detected by the external optical tracking apparatus.

The optical tracking device 50 may be embodied by an optical tracking system (OTS) to recognize optical markers such as the first and second optical markers 22 and 32, and the reference optical marker 40. A commercial medical OTS provides a function of transformation between the optical marker and the coordinate system as well as a distance to the optical marker, cardinal points and height, and therefore the commercial medial OTS may be employed as the optical tracking device 50.

The display 60 is to show an X-ray image captured by the detector 16 to a surgical operator, and the user interface 70 is to receive location information input by the surgical operator through, for example, a touch screen, a mouse, etc. The input location information may be displayed on the display 60 while overlapping with the displayed X-ray image.

The matcher 80 calculates a matching relationship between image pixels and 3D space coordinates, based on the coordinate systems of the first and second optical markers 22 and 32 obtained by the optical tracking device 50, the reference coordinate system of the reference optical marker 40 and the image captured by the detector 16. The matcher 80 may be embodied by a processor, a memory and software for performing an image processing process based on the coordinate systems.

Figure 3:
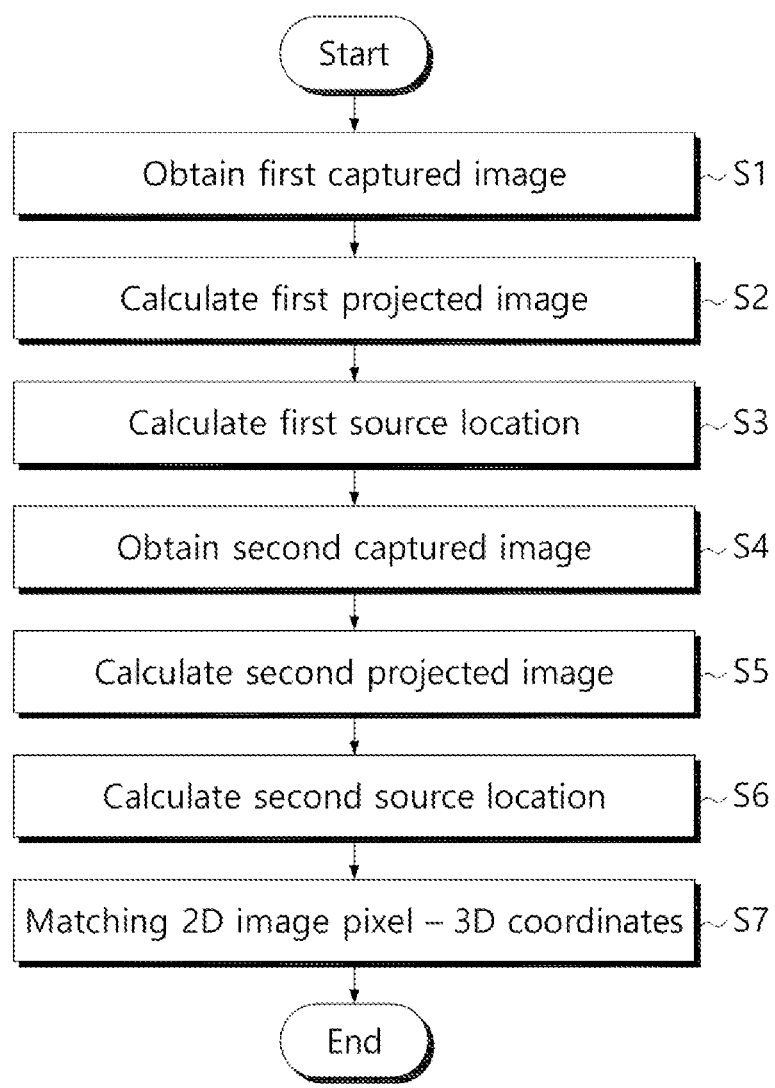
FIG. 3 is a flowchart of a matching method between 2D image pixels and 3D space coordinates according to an embodiment of the disclosure.

FIG. 3 is a flowchart of a matching method between 2D image pixels and 3D space coordinates according to an embodiment of the disclosure, and FIGS. 4 to 7 are schematic views for describing the matching method step by step according to an embodiment of the disclosure.

With reference to FIGS. 3 to 7, operations of the medical imaging system and the matcher 80 disclosed in FIG. 2 will be described in detail.

First, in the state that the C-arm source 14 and the detector 16 are in the first location, the source 14 emits an X-ray to a patient's lesion and the detector 16 obtains a first captured image (S1). Here, the first location refers to any location that is selectable by a surgical operator. Because an anterior-posterior (AP) image and a lateral-lateral (LL) image are needed on a surgical process, a location at which the AP image is obtainable is selected in this embodiment. However, the AP image is not accurately required in this embodiment. Therefore, the first location may be a location at which a similar image approximate to the AP image is obtainable, and the images captured at this location will be collectively called the AP image. Based on the first location, the X-ray emitted from the X-ray source 14 given as a point source goes through a subject along the first X-ray path and is then input to the detector 16, and the detector 16 obtains the first captured image, i.e., the AP image. The surgical operator does not have to capture a plurality of images to get the exact AP location, and therefore ease of use is significantly improved.

The matcher 80 obtains a first projected image by projecting the first captured image back to the first plate 20 along the X-ray path (S2). Here, the first ball marker located on the first captured image and the first ball marker located on the first plate 20 are matched to a 'reference point', thereby obtaining the first projected image.

Because the path of the first X-ray emitted from the X-ray source 14 given as the point source is expanded in the form of a cone, a well-known image warping algorithm may be applied to the first captured image so as to obtain the first projected image based on nonlinear transformation. Here, the location of the first ball marker on the first plate 20 of the same plane as the first projected image and the location of the first ball marker formed on the first captured image are matched to the reference point, and other pixels on the first captured image are subjected to linear or nonlinear interpolation, thereby obtaining the first projected image.

Figure 4:
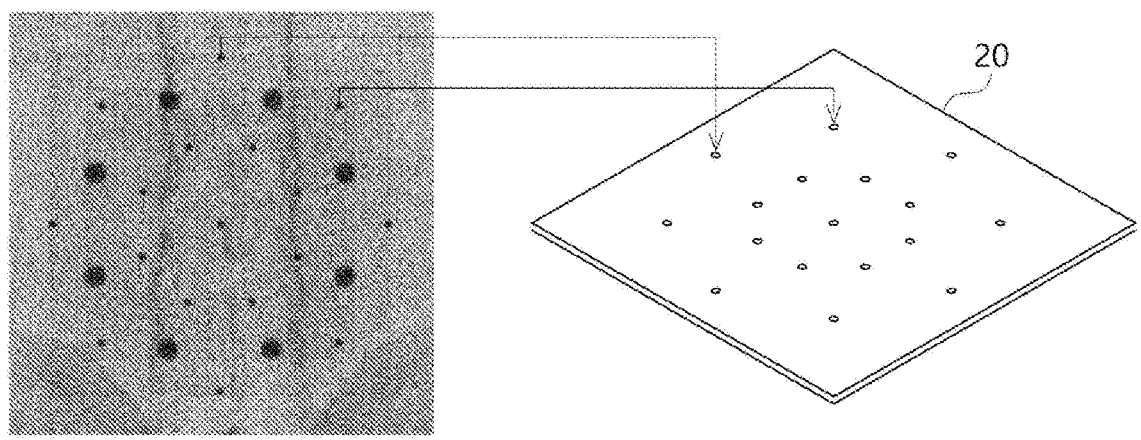
FIGS. 4 to 8 are schematic views for describing a matching process according to an embodiment of the disclosure.

For example, as disclosed in FIG. 4, a transformation matrix is obtained with reference to the first ball marker of the first plate 20, using on 'rigid body landmark transform' (see "Closed-form solution of absolute orientation using unit quaternions" written by Berthold K. P. Horn, included in Journal of the Optical Society of America A. 4:629-642), and data interpolation and smoothing are performed based on a spline curve using 'thin plate spline transform' (see "Splines minimizing rotation invariant semi-norms in Sobolev spaces" written by J. Duchon—constructive theory of functions of several variables, oberwolfach 1976), thereby transforming the first captured image, i.e., the AP image into the first projected image.

By the transformation matrix, which defines a transformation relationship between the first captured image and the first projected image, a certain pixel of the first captured image may be transformed into a pixel of the first projected image, and the pixel of the first projected image may be transformed into coordinates on the medical spatial reference coordinate system by means of the first optical marker 22 of the first plate 20.

Next, the matcher 80 obtains the location of the C-arm source 14 with regard to the first captured image (hereinafter, referred to as a 'first source location'), based on a relationship between the second ball marker located on the first projected image and the second ball marker on the second plate 30 (S3). Here, instead of the first captured image of which location information is unknown, the first projected image of which 3D location coordinates are known through the first optical marker 22 is used as reference.

Figure 5:
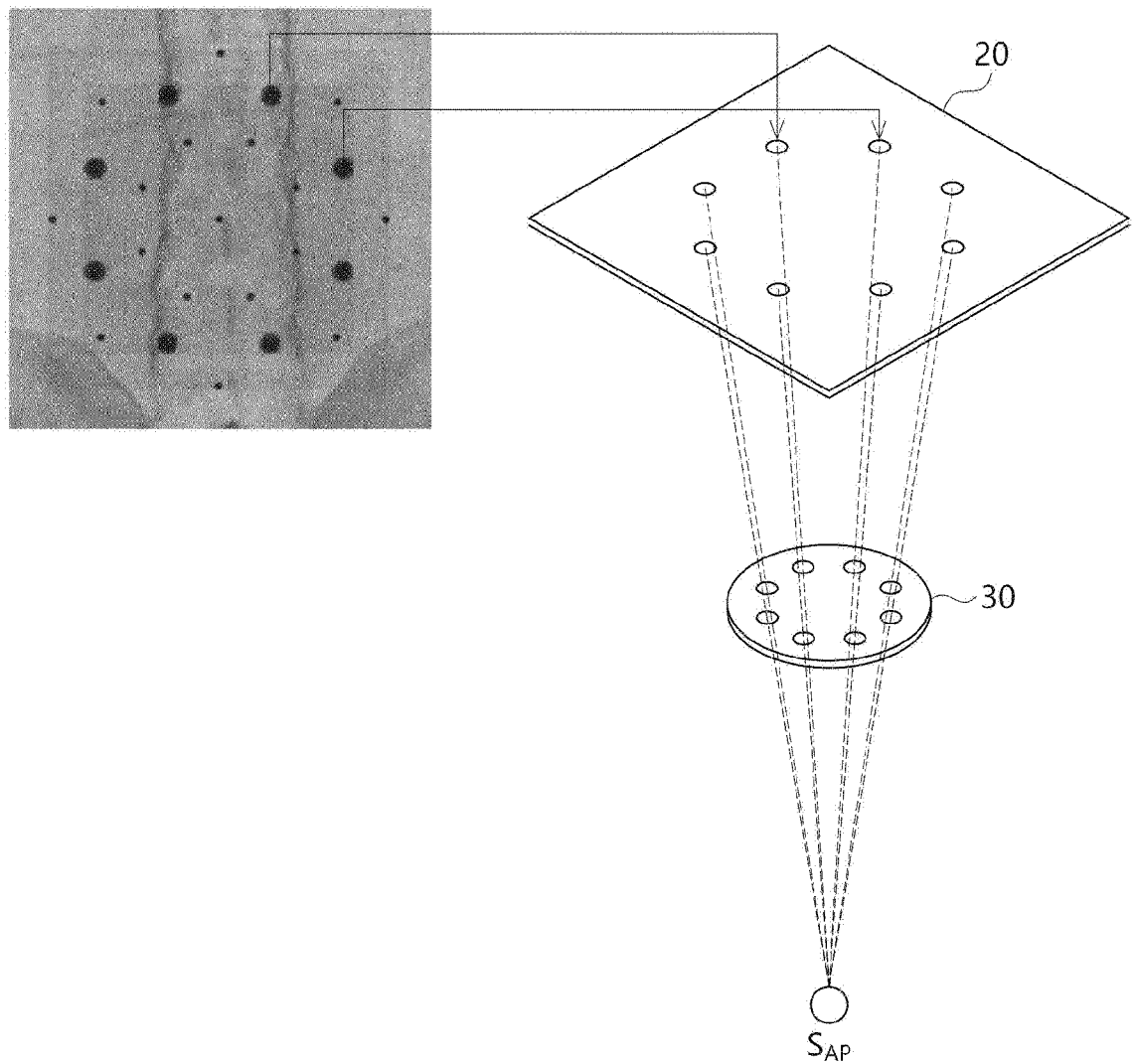

Referring to FIG. 5, the second ball markers on the first captured image are warped onto the first projected image, and then the locations of the second ball markers on the first projected image and the locations of the second ball markers on the second plate 30 are connected, thereby obtaining the first source location SAP at a point where the extended lines are intersected. Because the location information of the first projected image and the location information of the second plate 30 are obtained by the optical tracking device 50, it is possible to calculate the first source location SAP.

Next, in the state that the C-arm source 14 and the detector 16 are in the second location, the source 14 emits the X-ray to the patient's lesion and the detector 16 obtains a second captured image (S4). Here, the second location refers to any location that is selectable by a surgical operator, but is selected in this embodiment as a location for obtaining the LL image. However, the LL image is not accurately required in this embodiment. Therefore, the second location may be a location at which an image approximate to the LL image is obtainable, and the images captured at the second location will be collectively called the LL image.

The matcher 80 obtains a second projected image by projecting the second captured image back to the first plate 20 along the second X-ray path (S5). Like the same method as that in the operation S2, the plurality of first ball markers located on the second captured image and the first ball markers on the first plate 20 are matched to the 'reference point,' thereby obtaining the second projected image, in which the well-known image warping algorithm may be employed.

The matcher 80 obtains the location of the C-arm source 14 corresponding to the second location (hereinafter, referred to as a 'second source location'), based on a relationship in location between the second ball marker located on the second projected image and the second ball marker on the second plate 30 (S6).

Figure 6:
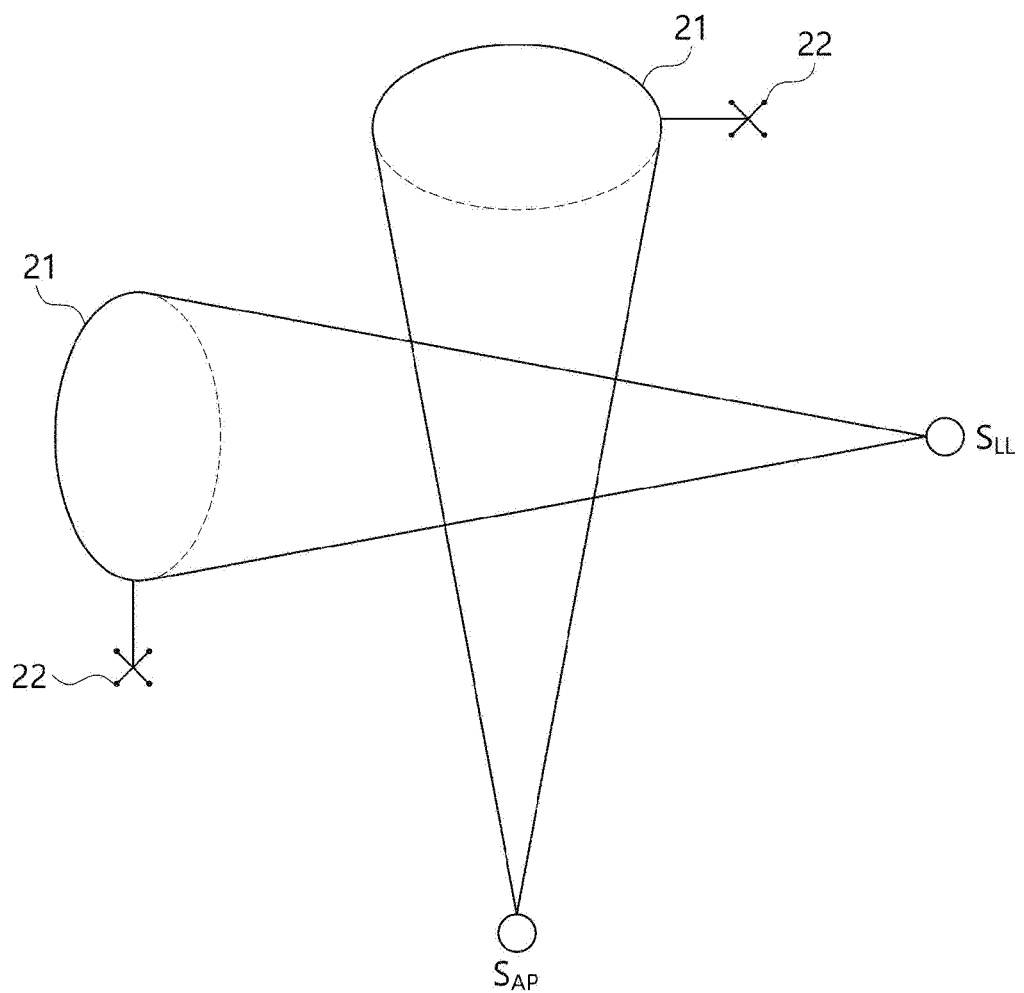

FIG. 6 shows a space in which the first X-ray conically extended from the first source location SAP up to the first plate 20, and the second X-ray conically extended from the second source location SLL up to the first plate 20 are overlapped. This overlapped space (hereinafter, referred to as an 'imaging space') refers to concept of a space in which pixels of interest on the first and second projected images are located or a 3D imaging space in which the subject is located.

Next, the matcher 80 matches the coordinates in the imaging space and the pixels on the captured image (S7).

Figure 7:
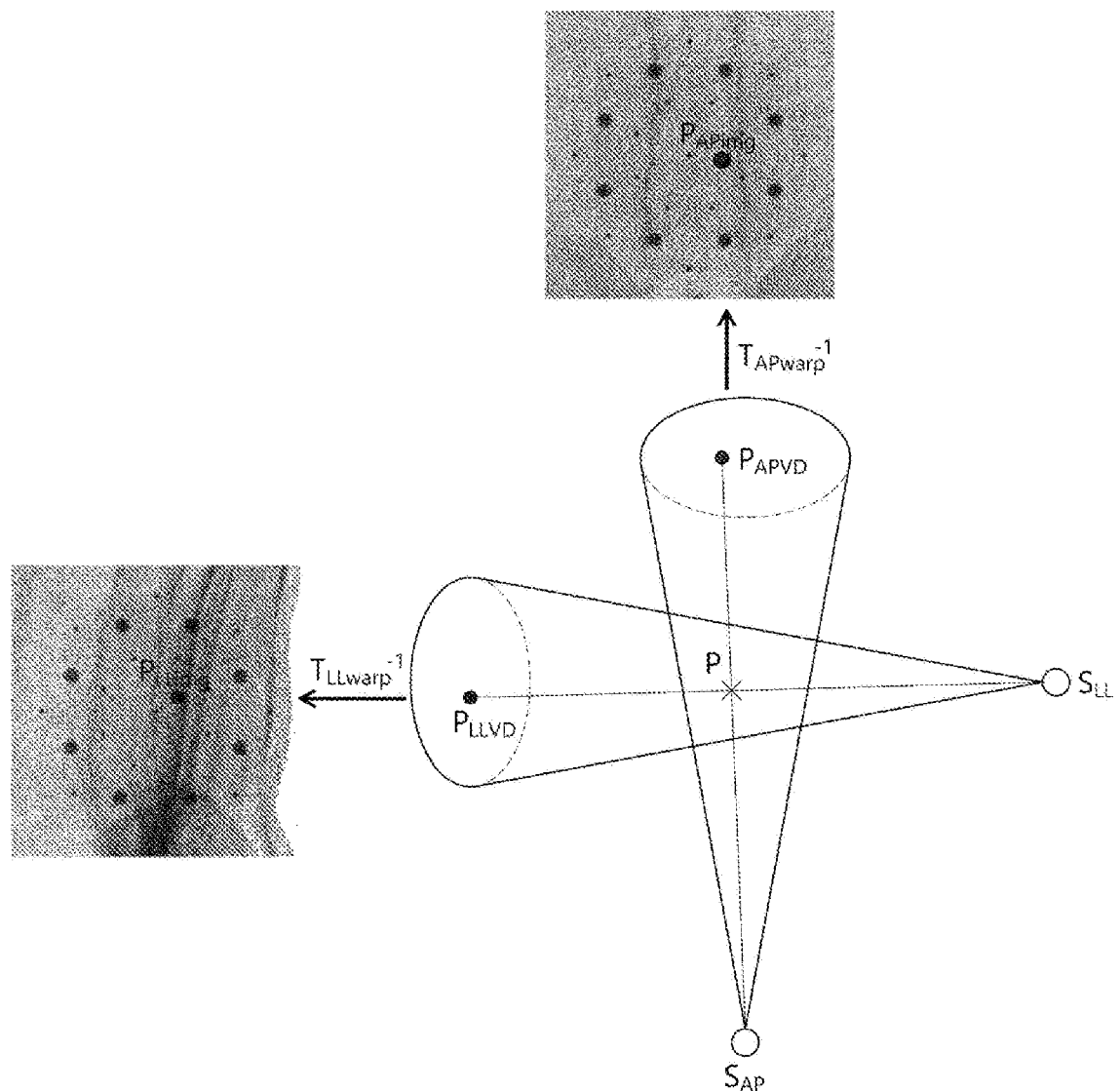

As disclosed in FIG. 7, certain coordinates P in the imaging space are matched to a first pixel $P_{APVD}$ obtained as projected to the first projected image by the first X-ray and a second pixel $P_{LLVD}$ obtained as projected to the second projected image by the second X-ray, and the first and second pixels ($P_{APVD}$, $P_{LLVD}$) on the first and second projected images are matched to pixels $P_{APimg}$ and $P_{LLimg}$ on the first and second captured images by inverse warping matrix $T_{APwarp}^{-1}$ and displayed on the display 60.

Here, a certain pixel in the imaging space may for example indicate a location at the tip of a surgical tool. The optical tracking device 50 may obtain coordinates, i.e., location information about the tip by recognizing a third optical marker of the surgical tool, and the matcher 80 may calculate the location of the tip on the first and second captured images based on the coordinates of the tip so as to display the location of the tip on the display 60. Therefore, the surgical operator can use a tracking function and a navigation function with the location of the surgical tool being displayed on two given 2D images in real time.

Figure 8:
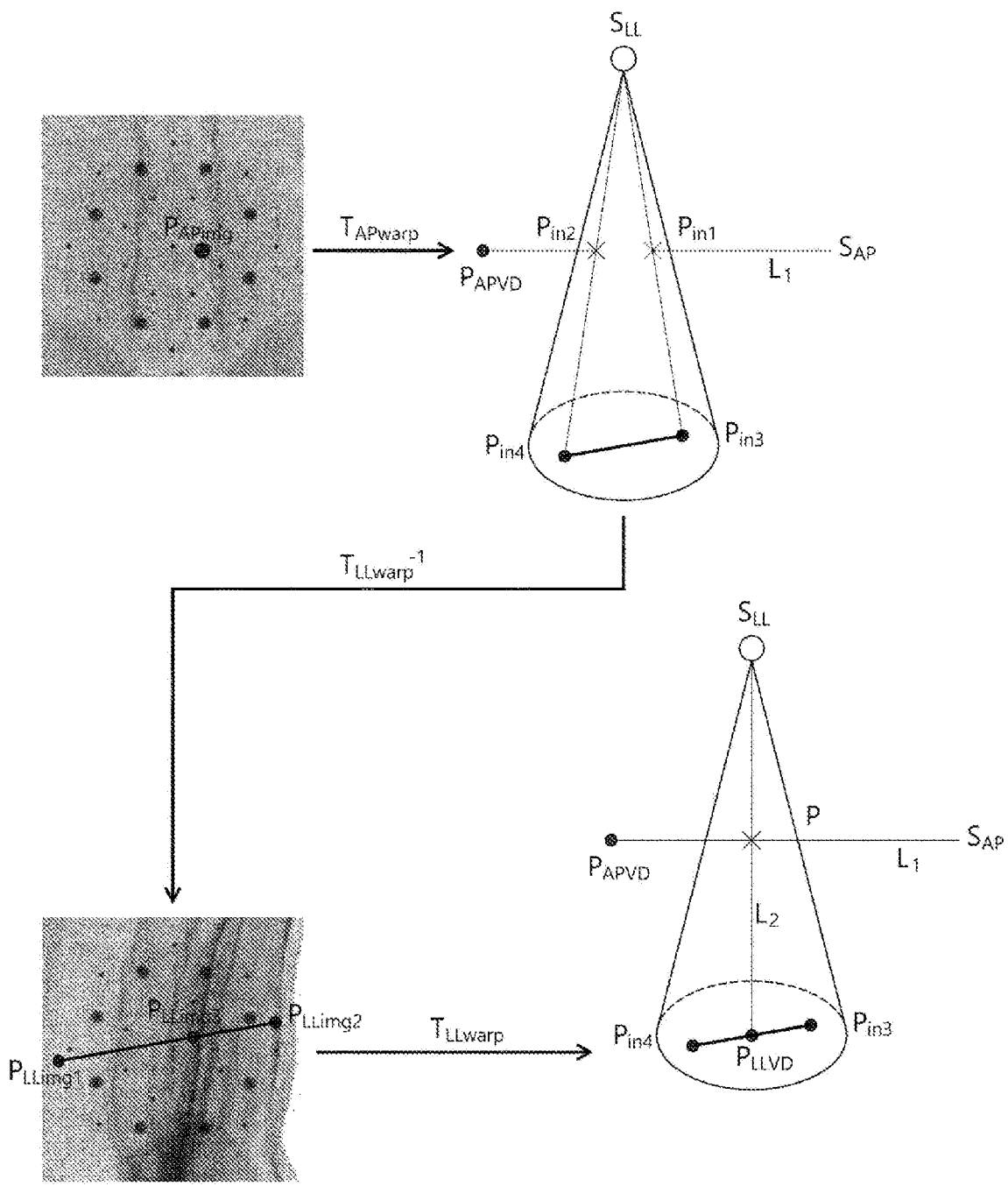

FIG. 8 shows that the first interest pixel $P_{APimg}$ on the first captured image and the corresponding second interest pixel $P_{LLimg}$ on the second captured image warped onto the first and second projected images and matched to certain coordinates P in the imaging space as back-projected forming an intersection P in the imaging space.

Specifically, a first line $P_{in2\text{-}Pin1}$ intersecting the imaging space is formed based on the back-projection from the first pixel $P_{APVD}$ on the first projected image corresponding to the first interest pixel $P_{APimg}$ on the first captured image toward the source 14 along the first X-ray path. The first line $P_{in2\text{-}Pin1}$ from the imaging space is matched to a line $P_{in4\text{-}Pin3}$ on the second projected image, and matched again to a line $P_{LLimg1}\text{-}P_{LLimg2}$ on an inverse warping $T_{LLwarp}^{-1}$ second captured image, so that the surgical operator can select a second interest pixel $P_{LLimg3}$ among the pixels on the matched line $P_{LLimg1}\text{-}P_{LLimg2}$ on the selected second captured image. The second interest pixel $P_{LLimg3}$ is warped onto the second projected image and matched to a certain pixel $P_{LLVD}$, and thus calculated as coordinates to which certain coordinates corresponding to the intersection P between the second interest pixel $P_{LLimg3}$ and the first interest pixel $P_{APimg}$ in the image space are matched.

The first interest pixel $P_{APimg}$ and the second interest pixel $P_{LLimg3}$ may be selected by the surgical operator as a point checked as the same feature point of the subject. Therefore, it will be understood that the surgical operator can select a desired point as the first interest pixel $P_{APimg}$ and the second interest pixel $P_{LLimg3}$ on the first captured image and the second captured image through the user interface 70, and this selected point may be transformed into spatial coordinates and provided as surgical planning information to a medical robot or the like.

Although a few embodiments of the disclosure have been described, it is understood by a person having ordinary knowledge in the art to which the disclosure pertains that change or replacement can be made in the embodiments of the disclosure without departing from technical scope of the disclosure.

For example, the locations where the first plate 20 and the second plate 30 are stationarily installed may be changeable within a range of intersecting the X-ray path, and the shapes and patterns of the markers on the first and second plates 20 and 30 may be selected within a range for achieving the same function and purpose.

Further, the matching steps of the flowchart shown in FIG. 3 may be changeable in precedence except a case where logical order between them is established. The two images are employed in the foregoing embodiments, but more images may be used in the matching.

Therefore, it is appreciated that the foregoing embodiments of the disclosure are for illustrative purposes only, and the scope of the disclosure are within the technical concept defined in the appended claims and its equivalents.

The invention claimed is:

1. A medical imaging system comprising:
   a C-arm comprising an X-ray source and a detector;
   a first plate placed on an X-ray path between the X-ray source and the detector, and comprising a first transmissive surface having a plurality of first ball markers configured to block X-rays, and a first optical marker used for calculating locations of the plurality of first ball markers;

a second plate placed on the X-ray path between the X-ray source and the detector, and comprising a second transmissive surface having a plurality of second ball markers configured to block X-rays, and a second optical marker used for calculating locations of the plurality of second ball markers;

a reference optical marker configured to provide a 3D reference coordinate system;

an optical tracking device configured to recognize locations of the first optical marker, the second optical marker, and the reference optical marker; and a matcher configured to calculate a matching relationship between coordinates on the 3D reference coordinate system and locations on a first captured image and a second captured image, based on the first captured image and the second captured image that are respectively obtained by the detector with regard to a subject while the detector is located at a first location and a second location, locations of a first ball marker and a second ball marker on the first captured image and a first ball marker and a second ball marker on the second captured image, and location information obtained by the optical tracking device.

2. The medical imaging system of claim 1, wherein the matcher is configured to obtain a first projected image and a second projected images by respectively projecting the first captured image and the second captured image to the first plate along the X-ray path, based on a matching relationship between the locations of the first ball marker on the first captured image and the first ball marker on the second captured image, and the location of the respective first ball marker on the first plate calculated using the first optical marker.

3. The medical imaging system of claim 2, wherein the matcher is configured to obtain a first source location and a second source location of the X-ray source respectively corresponding to the first captured image and the second captured image, based on a matching relationship between locations of a second ball marker on the first projected image and a second ball marker on the second projected image, and the location of the respective second ball marker on the second plate calculated using the second optical marker.

4. The medical imaging system of claim 3, wherein the matcher is configured to calculate a 3D imaging space in which a projection path of a first X-ray overlaps a projection path of a second X-ray, the projection path of the first X-ray is a projection path of X-ray emitted from the first source location to the first plate based on a location relationship between the first source location and the first projected image, and the projection path of the second X-ray is a projection path of X-ray emitted from the second source location to the first plate based on a location relationship between the second source location and the second projected image.

5. The medical imaging system of claim 1, further comprising:

a display configured to display the first captured image and the second captured image; and a user interface configured to receive location information about locations on the first captured image and the second captured image from a surgical operator, wherein the matcher is configured to calculate spatial coordinates in the reference coordinate system, the spatial coordinates corresponding to the location information input by the surgical operator.

6. The medical imaging system of claim 1, further comprising a medical instrument comprising a third optical marker, wherein the matcher is configured to obtain location coordinates of the medical instrument obtained by the optical tracking device using the third optical marker, and calculate location information about the medical instrument on the first captured image and the second captured image based on the matching relationship.

7. The medical imaging system of claim 1, wherein the first plate comprises a fastening member to be fastened to the C-arm so that the first transmissive surface is to be located in front of the detector.

8. The medical imaging system of claim 1, wherein the second plate is placed between the first plate and the X-ray detector.

9. A method of matching a C-arm 2D image and a 3D space, performed by a medical imaging system, comprising:

obtaining a first captured image at a first location by a C-arm detector of the medical imaging system;

obtaining, by a matcher of the medical imaging system, a first projected image by projecting the first captured image back to a first plate along a first X-ray path corresponding to the first location, wherein the first plate is provided on the first X-ray path and comprises a first optical marker of which a location is identifiable in a reference coordinate system;

calculating, by the matcher, a first source location of a C-arm source corresponding to the first location based on a matching relationship between a location on the reference coordinate system of a ball marker of a second plate provided on the first X-ray path and a location of the ball marker of the second plate on the first projected image;

obtaining a second captured image at a second location by the C-arm detector;

obtaining, by the matcher, a second projected image by projecting the second captured image back to the first plate provided on a second X-ray path along the second X-ray path corresponding to the second location;

calculating, by the matcher, a second source location of the C-arm source corresponding to the second location based on a matching relationship between a location on the reference coordinate system of the ball marker of the second plate provided on the second X-ray path and a location of the ball marker of the second plate on the first projected image; and calculating, by the matcher, coordinates of an intersection between a first line connecting the first source location and a first pixel on the first projected image and a second line connecting the second source location and a second pixel on the second projected image.

10. The method of claim 9, wherein the obtaining the first projected image of the first captured image on the first plate by the matcher comprises calculating the first projected image by warping the first captured image based on a location on the first captured image corresponding to a ball marker of the first plate and a location on the reference coordinate system.

11. The method of claim 9, wherein the obtaining the second projected image of the second captured image on the first plate by the matcher comprises calculating the second projected image by warping the second captured image based on a location on the second captured image corresponding to a ball marker of the first plate and a location on the reference coordinate system.

12. A method of matching a C-arm 2D image and a 3D space, performed by a medical imaging system, comprising:

obtaining a first captured image at a first location by a C-arm detector of the medical imaging system;

obtaining, by a matcher of the medical imaging system, a first projected image by projecting the first captured image back to a first plate along a first X-ray path corresponding to the first location, wherein the first plate is provided on the first X-ray path and comprises a first optical marker of which a location is identifiable in a reference coordinate system;

calculation, by the matcher, a first source location of a C-arm source corresponding to the first location based on a matching relationship between a location on the reference coordinate system of a ball marker of a second plate provided on the first X-ray path and a location of the ball marker of the second plate on the first projected image;

obtaining a second captured image at a second location by the C-arm detector;

obtaining, by the matcher, a second projected image by projecting the second captured image back to the first plate provided on a second X-ray path along the second X-ray path corresponding to the second location;

calculating, by the matcher, a second source location of the C-arm source corresponding to the second location based on a matching relationship between a location on the reference coordinate system of the ball marker of the second plate provided on the second X-ray path and a location of the ball marker of the second plate on the first projected image; and calculating, by the matcher, first pixels to which spatial coordinates are projected on the first projected image along the first X-ray path, and calculating second pixels to which the spatial coordinates are projected on the second projected image along the second X-ray path.

13. The method of claim 12, wherein the obtaining the first projected image of the first captured image on the first plate by the matcher comprises calculating the first projected image by warping the first captured image based on a location on the first captured image corresponding to a ball marker of the first plate and a location on the reference coordinate system.

14. The method of claim 12, wherein the obtaining the second projected image of the second captured image on the first plate by the matcher comprises calculating the second projected image by warping the second captured image based on a location on the second captured image corresponding to a ball marker of the first plate and a location on the reference coordinate system.

* * * * *